US011464409B2

(12) United States Patent
Orlowski et al.

(10) Patent No.: US 11,464,409 B2
(45) Date of Patent: Oct. 11, 2022

(54) OPTICAL COHERENCE TOMOGRAPHIC APPARATUS AND METHOD FOR THE SAME

(71) Applicant: CANON KABUSHIKI KAISHA, Tokyo (JP)

(72) Inventors: Slawomir Orlowski, Toruń (PL); Pawel Dalasinski, Toruń (PL); Tomasz Bajraszewski, Głogowo (PL)

(73) Assignee: CANON KABUSHIKI KAISHA, Tokyo (JP)

( * ) Notice: Subject to any disclaimer, the term of this patent is extended or adjusted under 35 U.S.C. 154(b) by 405 days.

(21) Appl. No.: 16/804,778

(22) Filed: Feb. 28, 2020

(65) Prior Publication Data
US 2020/0196857 A1  Jun. 25, 2020

Related U.S. Application Data

(63) Continuation of application No. PCT/JP2018/032589, filed on Sep. 3, 2018.

(30) Foreign Application Priority Data

Sep. 6, 2017  (JP) .............................. JP2017-171186

(51) Int. Cl.
*A61B 3/10*  (2006.01)
*A61B 3/00*  (2006.01)
(Continued)

(52) U.S. Cl.
CPC ............ *A61B 3/102* (2013.01); *A61B 3/0025* (2013.01); *A61B 3/0058* (2013.01);
(Continued)

(58) Field of Classification Search
CPC ..... A61B 3/102; A61B 3/0025; A61B 3/0058; A61B 3/1225; A61B 3/152; G01B 9/0203; G01B 9/02091; G01B 2290/65
See application file for complete search history.

(56) References Cited

U.S. PATENT DOCUMENTS

2009/0303438 A1    12/2009  Yamada
2010/0039616 A1 *   2/2010  Yumikake .......... G01N 21/4795
                                                351/221

(Continued)

FOREIGN PATENT DOCUMENTS

JP    2009-291252 A    12/2009
JP    2011-245183 A    12/2011
JP    2016-10658 A      1/2016

*Primary Examiner* — Jonathan M Hansen
(74) *Attorney, Agent, or Firm* — Canon U.S.A., Inc. IP Division

(57) ABSTRACT

An optical coherence tomography apparatus includes a control unit configured, before a tomographic image to be stored is obtained using the output from the light receiving unit during a period in which the measurement light is scanned in a first scanning pattern for scanning an image capturing region of the subject eye, to control the optical scanning unit so as to repeatedly scan the measurement light in a second scanning pattern for scanning the measurement light over at least part of the image capturing region in a scanning time shorter than a scanning time of the first scanning pattern and to control the driving unit so as to drive the focusing unit using the output from the light receiving unit during a period in which the measurement light is repeatedly scanned in the second scanning pattern.

13 Claims, 14 Drawing Sheets

(51) Int. Cl.
*A61B 3/12* (2006.01)
*A61B 3/15* (2006.01)
*G01B 9/02015* (2022.01)
*G01B 9/02091* (2022.01)

(52) U.S. Cl.
CPC ............ *A61B 3/1225* (2013.01); *A61B 3/152* (2013.01); *G01B 9/0203* (2013.01); *G01B 9/02091* (2013.01)

(56) References Cited

U.S. PATENT DOCUMENTS

| | | |
|---|---|---|
| 2014/0268039 A1 | 9/2014 | Arianta |
| 2015/0230987 A1* | 8/2015 | Friedman ............ A61F 9/00825 606/6 |
| 2015/0313467 A1 | 11/2015 | Sakai |
| 2015/0374228 A1 | 12/2015 | Satake |
| 2019/0274541 A1* | 9/2019 | Higuchi ............... A61B 5/0066 |

* cited by examiner

FIG. 17A

| MAIN IMAGING SCANNING PATTERN | PRESCANNING PATTERN 1 | PRESCANNING PATTERN 2 |
|---|---|---|
| 3D SCANNING | CENTRAL CROSS-SHAPE AND UPPER-AND-LOWER-LINE PATTERN | DIAGONAL SCANNING |
| RADIAL SCANNING | CROSS-SHAPED SCANNING | CIRCULAR SCANNING |
| MULTI CROSS-SHAPED SCANNING | CROSS-SHAPED SCANNING | CIRCULAR SCANNING |
| CROSS-SHAPED SCANNING | CROSS-SHAPED SCANNING | ONE-LINE SCANNING |

FIG. 17B

| MAIN IMAGING SCANNING PATTERN | PRESCANNING PATTERN 1 | PRESCANNING PATTERN 2 |
|---|---|---|
| 3D SCANNING | HORIZONTAL THREE-LINE PATTERN | DIAGONAL (CENTER) SCANNING |
| RADIAL SCANNING | CROSS-SHAPED SCANNING | CROSS-SHAPED SCANNING |
| MULTI CROSS-SHAPED SCANNING | CROSS-SHAPED SCANNING | CROSS-SHAPED SCANNING |
| CROSS-SHAPED SCANNING | CROSS-SHAPED SCANNING | ONE-LINE SCANNING |

OPTICAL COHERENCE TOMOGRAPHIC APPARATUS AND METHOD FOR THE SAME

CROSS-REFERENCE TO RELATED APPLICATIONS

This application is a Continuation of International Patent Application No. PCT/JP2018/032589, filed Sep. 3, 2018, which claims the benefit of Japanese Patent Application No. 2017-171186, filed Sep. 6, 2017, both of which are hereby incorporated by reference herein in their entirety.

TECHNICAL FIELD

The present invention relates to an optical coherence tomography apparatus and a method for controlling the same.

BACKGROUND ART

A standard optical coherence tomography apparatus (hereinafter referred to as "OCT apparatus") includes a fundus imaging unit configured to generate a fundus image of the subject eye and an OCT imaging unit configured to execute OCT examination. These units generally each include a focusing unit (a focus lens) for correcting a refractive error in the subject eye to focus in the fundus to be observed. The driving of the focusing unit is controlled by a control unit that controls the entire apparatus (driven by a motor).

A typical example of the fundus imaging unit is a confocal scanning laser ophthalmoscope (hereinafter referred to as "SLO unit"), which has an image capturing region wider than the image capturing region of the OCT imaging unit. For example, in recent OCT apparatuses, the image capturing region of the SLO unit is about 10×10 mm, and the image capturing region of the OCT unit is 3×3 mm, which is part of the image capturing region of the SLO unit. The image capturing region of the OCT unit is usually variable in the image capturing region of the SLO unit.

In general, focusing is an operation performed in common among ophthalmic imaging apparatuses to maximize the sharpness and contrast of the eye-fundus image to be obtained. In the above apparatus configuration, the focusing is executed by the user giving an adjustment instruction to the control unit while observing an eye-fundus image displayed on a display 350 to drive the focusing unit.

OCT apparatuses are increasingly required to have a function to automatically perform the focusing operation, that is, an autofocus function, to simplify an operation to increase the examination throughput, as well as to enhance the reproducibility of the examination result. There is a known technique for automatizing the above manual operation to detect the focus state of the OCT unit (PTL 1).

PTL 1 discloses a technique for properly performing focus adjustment on a tomographic image by performing first autofocusing of the OCT unit using a focus signal from the SLO unit and then performing second autofocusing of the OCT unit based on a tomographic image obtained by the OCT unit. Specifically, the first autofocusing is to detect the in-focus position of the SLO unit using the features of the confocal type that the contrast and the image output level are maximized and to control the OCT focusing unit based on the detected in-focus position. The second autofocusing is to obtain a tomographic image at a plurality of focal positions and to control the OCT focusing unit using, as the in-focus position, a focal position at which the contrast and so on of the obtained tomographic image is highest. After completion of the autofocusing of the OCT unit, a tomographic image to be stored is obtained by the OCT unit.

PTL 1 discloses that a scanning pattern for scanning measurement light for obtaining a tomographic image for autofocusing and a scanning pattern for scanning measurement light for obtaining a tomographic image to be stored are the same scanning pattern for scanning in the same shape (linearly) and in the same direction.

CITATION LIST

Patent Literature

PTL 1 Japanese Patent Laid-Open No. 2009-291252

SUMMARY OF INVENTION

An optical coherence tomography apparatus according to an aspect of the present invention includes an interference optical system including a light receiving unit configured to receive interference light of returned light from a subject eye irradiated with measurement light and reference light corresponding to the measurement light, a tomographic-image obtaining unit configured to obtain a tomographic image of the subject eye using an output from the light receiving unit, an optical scanning unit disposed in the interference optical system and configured to scan the subject eye with the measurement light, a driving unit disposed in the interference optical system and configured to drive a focusing unit, a control unit configured, before a tomographic image to be stored is obtained using the output from the light receiving unit during a period in which the measurement light is scanned in a first scanning pattern for scanning an image capturing region of the subject eye, to control the optical scanning unit so as to repeatedly scan the measurement light in a second scanning pattern for scanning the measurement light over at least part of the image capturing region in a scanning time shorter than a scanning time of the first scanning pattern and to control the driving unit so as to drive the focusing unit using the output from the light receiving unit during a period in which the measurement light is repeatedly scanned in the second scanning pattern.

Further features of the present invention will become apparent from the following description of exemplary embodiments with reference to the attached drawings.

BRIEF DESCRIPTION OF DRAWINGS

FIG. 17A is a table illustrating main imaging scanning patterns and prescanning patterns.

FIG. 17B is a table illustrating main imaging scanning patterns and prescanning patterns.

DESCRIPTION OF EMBODIMENTS

Figure 1:
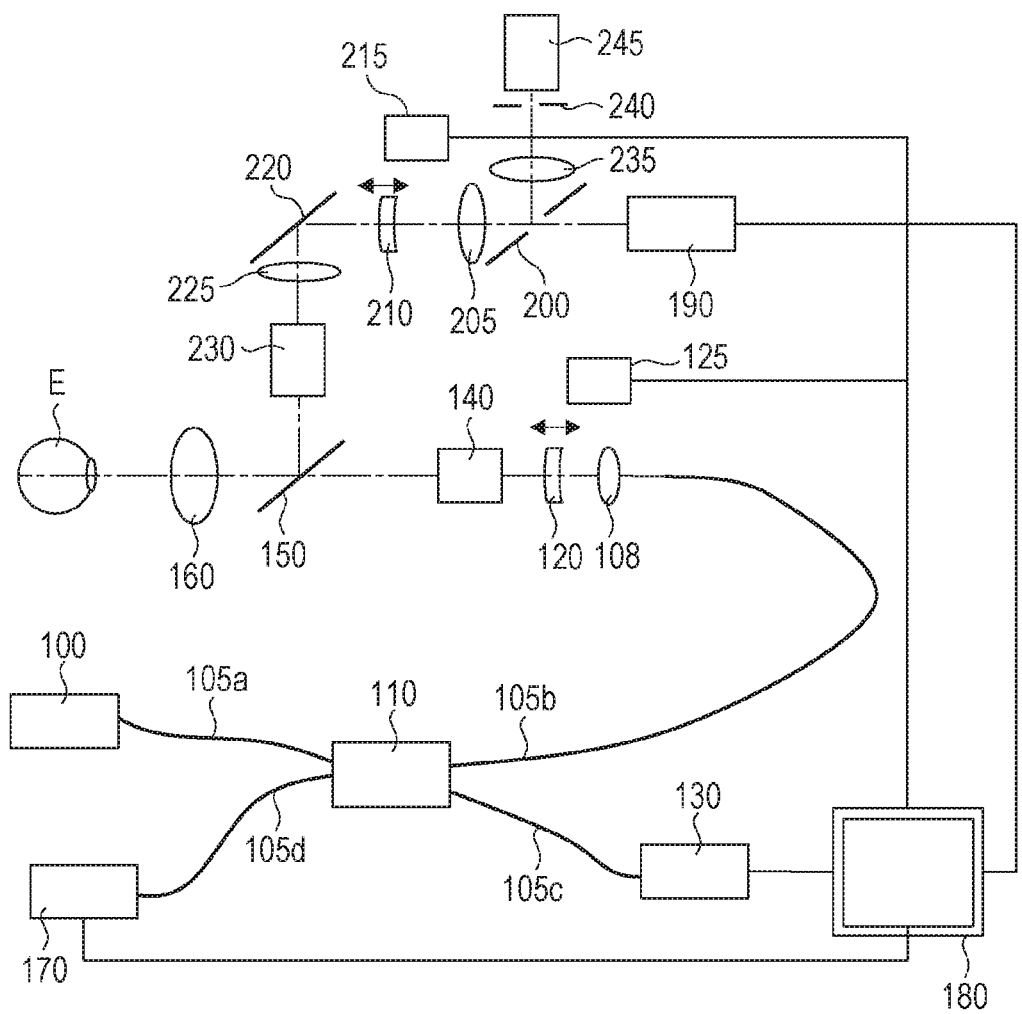
FIG. 1 is a diagram illustrating the configuration of a two-dimensional scanning spectral-domain optical coherence tomography (SD-OCT) apparatus according to an embodiment of the present invention.

When the scanning pattern for scanning measurement light for obtaining a tomographic image for autofocusing is the same as the scanning pattern for scanning measurement light for obtaining a three-dimensional tomographic image to be stored, as in the related art, the in-focus state of the OCT unit needs to be detected for each main scanning line. In other words, the calculation time in detecting the in-focus state of the OCT unit increases as the number of the main scanning lines of the scanning pattern for scanning measurement light for obtaining the tomographic image to be stored increases. This increases the time required for the autofocusing of the OCT unit. For this reason, the known technique for the autofocusing of the OCT unit is not practical.

Accordingly, an object of the present embodiment is to reduce the time required for the autofocusing of the OCT unit.

An optical coherence tomography apparatus according to an embodiment of the present invention includes a control unit configured, before a tomographic image to be stored is obtained using the output from the light receiving unit during a period in which the measurement light is scanned in a first scanning pattern for scanning an image capturing region of the subject eye, to control the optical scanning unit so as to repeatedly scan the measurement light in a second scanning pattern for scanning the measurement light over at least part of the image capturing region in a scanning time shorter than a scanning time of the first scanning pattern. At that time, the control unit controls the driving unit so as to drive the focusing unit using the output from the light receiving unit during a period in which the measurement light is repeatedly scanned in the second scanning pattern. This allows reducing, for example, the time required for the autofocusing of the OCT unit.

Embodiments of the present invention will be described with reference to the drawings. The same or similar components, members, processes illustrated in the drawings are denoted by the same reference signs, and duplicated descriptions will be omitted as appropriate. In the drawings, part of unimportant components, members, and processes may be omitted.

First Embodiment

Figure 2:
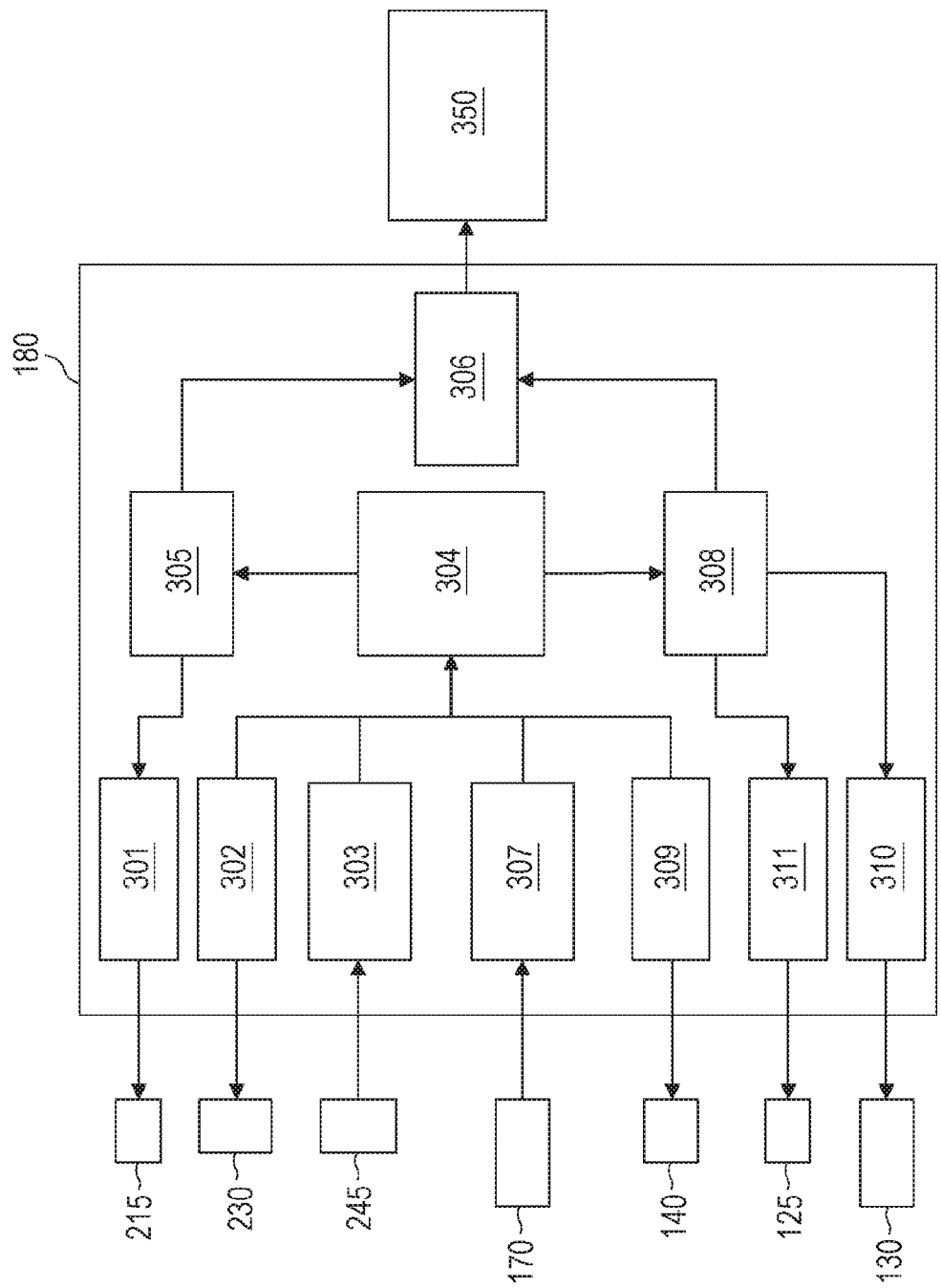
FIG. 2 is a diagram illustrating the configuration of a control/signal processing unit 180.

FIG. 1 is a diagram illustrating the configuration of an optical coherence tomography apparatus (an OCT apparatus) according to an embodiment of the present invention. FIG. 2 is a diagram illustrating the configuration of a control/signal processing unit 180 that controls the entire apparatus. The configuration of the OCT apparatus to which the present invention can be applied will be described with reference to FIGS. 1 and 2, taking a spectral-domain (SD)-OCT as an example.

OCT Unit: Interference Optical System

Measurement light that has exited from an OCT light source 100 that emits low coherence light passes through an optical fiber 105a and is split into measurement light and reference light by a light splitting unit 110. The obtained measurement light enters an optical fiber 105b and is guided, via the exit end core of the optical fiber 105b serving as a secondary light source, to an OCT focus lens 120 constituting an OCT focusing unit through a collimator lens 108. An optical scanning unit 140 including two galvanometric mirrors, a dichromatic mirror 150, and an objective lens 160 facing the subject eye E are provided behind the OCT focus lens 120 to guide the measurement light to the fundus of the subject eye E to be imaged. The position of the OCT focus lens 120 on the optical axis can be moved by a lens driving mechanism 125 according to a signal from an OCT focus control unit 311 in the control/signal processing unit 180. Adjusting the position allows compensating the refractive error of the target subject eye E to conjugate the exit end core of the optical fiber 105b and the fundus to be imaged. This adjusting operation is referred to as "OCT unit focusing". The optical scanning unit 140 and the pupil of the subject eye E are disposed in an optically conjugate relationship using the objective lens 160. Driving the two galvanometric mirrors according to a control signal output from an OCT scanning control unit 309 in the control/signal processing unit 180 at the right time allows the measurement light to operated in a given pattern on the fundus of the subject eye E.

The measurement light scattered and reflected by the subject eye fundus is referred to as returned light. The returned light passes back through the objective lens 160, the dichromatic mirror 150, the optical scanning unit 140, the OCT focus lens 120, and the collimator lens 108 and is guided by the optical fiber 105b again into the light splitting unit 110. The other measurement light split by the light splitting unit passes through an optical fiber 105c into a reference light path unit 130 forming a reflected light path in which the optical path length can be adjusted by a reference-light-path-length control unit 310 in the control/signal processing unit 180 and is returned to the light splitting unit 110. The reference light and the returned light coming through the optical fiber 105b are multiplexed into interference light by the light splitting unit 110 and is guided to a spectrometer 170 through an optical fiber 105d. The spectrometer 170 splits the incident interference light with, for example, a diffraction grating, detects the spectral component with a line sensor or the like (not illustrated), and outputs the detection result. The control/signal processing unit 180 reads the output from the spectrometer 170 via the second analog-to-digital (A/D) converter 307 and performs signal processing for obtaining a tomographic signal from a region on the subject eye fundus irradiated with the measurement light. To obtain a tomographic signal from a desired region, the optical scanning unit 140 is controlled to move the measurement light to the desired region continuously using the OCT scanning control unit 309 in the control/signal processing unit 180, and a plurality of tomographic signals obtained from the output of the spectrometer 170 are properly disposed using the control signal. This signal processing will be described later.

Fundus Observation Unit

An SLO unit serving as a fundus observation system is combined, in a wavelength separation form, to the optical path branching from the dichromatic mirror 150 behind the objective lens 160. An illumination beam emitted from a laser source 190 passes through the hole of a perforated mirror 200, a lens 205, an SLO focus lens 210, a mirror 220, and a lens 225, is guided to a second optical scanning unit 230 including two galvanometric mirrors, like the optical scanning unit 140, and is coupled to the optical axis of the objective lens 160 by the dichromatic mirror 150 to spot-illuminate the subject eye fundus. The light is scattered and reflected by the subject eye fundus to go back through the optical path to reach the perforated mirror 200. The light is then reflected by a peripheral reflecting portion, is then collected by a light-collecting lens 235, passes through a confocal aperture 240, and is received by a photoreceiver 245 like an avalanche photodiode.

Like the OCT focus lens 120, the position of the SLO focus lens 210 on the optical axis can be moved by a lens driving mechanism 215 which is controlled according to a control signal from an SLO focus control unit 301 in the control/signal processing unit 180. By adjusting the position, the confocal aperture 240 and the fundus of the subject eye E to be imaged are conjugated. This adjusting operation is referred to as "SLO unit focusing". The imaginary intersection of the perforated mirror 200 and the optical axis, the center of the optical deflection of the optical scanning unit 230, and the pupil of the subject eye E are optically conjugate. By the optical scanning unit 230 raster-scanning the illumination beam according to an output from an SLO scanning control unit 302 in the control/signal processing unit 180, the photoreceiver 245 sequentially obtains two-dimensional image information on the subject eye fundus. The control/signal processing unit 180 converts the output to a digital value with a first A/D converter 303 and stores the digital value in an image memory 304 in association with the raster scanning control signal sent to the optical scanning unit 230. An SLO image generation unit 305 reads the data to generate a two-dimensional eye-fundus image of the subject eye fundus and outputs the image to a display control unit 306 and also to the SLO focus control unit 301 as a feedback signal for SLO unit focusing.

OCT Image Reconfiguration

Likewise, the returned light from the subject eye fundus is converted to digital data, as an output signal obtained by resolving the light into wavelength components with the spectrometer 170, by the second A/D converter 307 in the control/signal processing unit 180 and is stored in the image memory 304 in association with the control signal from the optical scanning unit 140, which is measurement light irradiation position information. An OCT image generation unit 308, which is an example of the tomographic-image obtaining unit, performs dispersion compensation processing, wavelength-wavenumber conversion, Fourier transformation, and logarithmic conversion of the intensity of the optical system on the digital data to generate a depthwise luminance profile (an A-mode signal) at one point of the subject eye fundus. The OCT image generation unit 308 disposes the luminance profile according to a control signal from the optical scanning unit 140, which is irradiation position information on the measurement light associated therewith, to obtain a retina tomographic image. This is referred to as OCT image generation processing. Note that such signal processing for generating a depthwise luminance profile at one point of the subject eye fundus is a combination of complex computation processes, so that increasing the resolution and range of the image capturing will increase the time required.

Thus, the basic configuration and basic functions of the OCT unit have been described taking a what-is-called spectral domain OCT as an example. However, an OCT unit of the present invention is not limited to the above. Any OCT units that operate the imaging plane, such as a wavelength swept OCT and a line-scanning time domain OCT, have the same advantages.

Operating Procedure for OCT Apparatus

Next, the operating procedure for the OCT apparatus including the fundus observation unit and the OCT unit described above will be described with reference to a flowchart for the OCT imaging procedure in FIG. 3 and the display screen of the display 350 in FIG. 4. The examiner points and presses a start button 505 in FIG. 4 illustrating the display screen using, for example, a pointing device (not illustrated), to set the apparatus to a preview state for apparatus preparation operations. When preview is started, the SLO unit turns on the laser light source 190, drives the optical scanning unit 230 in the control/signal processing unit 180, and reads the output from the photoreceiver 245 into the image memory 304 in sequence, and the display control unit 306 outputs an SLO image 520, which is a two-dimensional image of the subject eye fundus, generated by the SLO image generation unit 305, to the display 350 (S100). The examiner aligns the apparatus to a position at which the optical axis of the objective lens 160 is coaxial with the pupil of the subject eye E and at which the optical scanning unit 230 and the optical scanning unit 140 conjugate while viewing an anterior eye image 510 of the subject eye E observed by an anterior eye observation unit (not illustrated) (S110). When the alignment is properly achieved, a two-dimensional image of the subject eye fundus is displayed on the lower left frame as the SLO image 520. An indicator 521 indicating a default OCT image capturing region is displayed on the two-dimensional image (S120).

SLO Focusing

Figure 5:
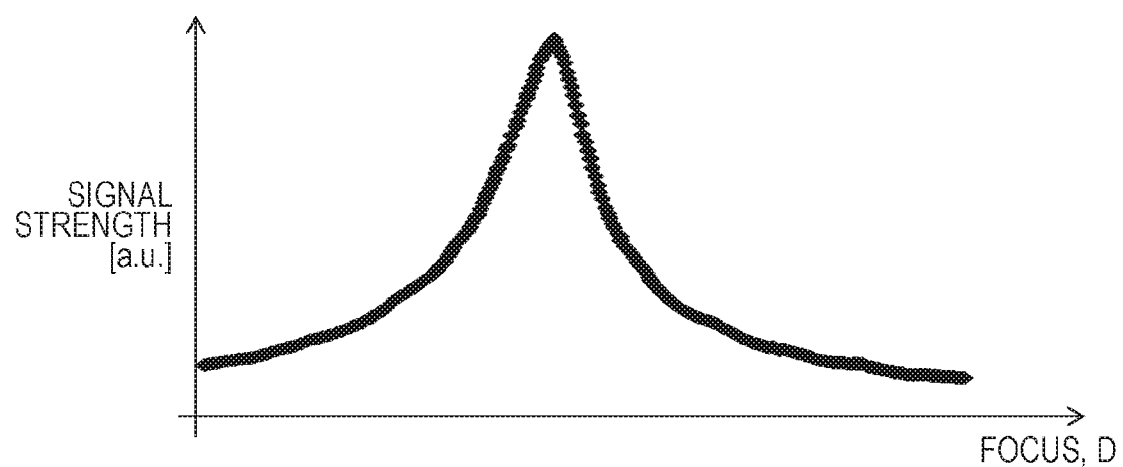
FIG. 5 is a graph illustrating a change in an evaluation value indicating the in-focus state of SLO.

When the examiner presses a switch 540 for starting SLO focusing with a pointing device or the like, SLO focusing is started (S130). First, the SLO focus control unit 301 in the control/signal processing unit 180 drives the lens driving mechanism 215 to move the SLO focus lens 210 to one end of the adjustment region. After moving the SLO focus lens 210 by a predetermined amount, the SLO focus control unit 301 evaluates the SLO images generated by the SLO image generation unit 305 in sequence to search for the in-focus position of the SLO unit. FIG. 5 is a graph illustrating a change in the evaluation value indicating the in-focus state of the SLO relative to the position of the SLO focus lens 210. For the evaluation function, for example, the average luminance of the SLO image in the OCT image capturing region 521 of the SLO image is used. Since the SLO unit is of the confocal system, as described above, the image has a maximum intensity when the subject eye fundus is in focus. Therefore, the evaluation function has a single peak at the position of the SLO focus lens 210 illustrated in FIG. 5.

Moving the SLO focus lens 210 to the peak position, the SLO focusing is completed. At that time, the OCT focus lens 120 in the OCT unit is preferably moved to the position corresponding to the SLO focus lens 210, as described in the section of the related art. The focusing may not necessarily be performed automatically. For example, the SLO focus lens 210 may be moved by operating a slide bar provided on one side of the SLO image with a pointing device, or alternatively, SLO focus adjustment may be started automatically without operating the SLO focusing start switch 540.

Upon confirmation of completion of the SLO focusing, the OCT unit turns on the OCT light source 100, and the OCT scanning control unit 309 in the control/signal processing unit 180 drives the optical scanning unit 140 so as to start OCT scanning in a prescanning pattern 1, which is an example of the first scanning pattern (S140). For example, when the main imaging scanning pattern is the rectangular 3D volume scanning pattern 521, a central cross-shape and upper-and-lower-line pattern composed of a cross shape at the center of the OCT image capturing region (rectangular) 521 and the upper and lower lines is selected for the prescanning pattern 1, as illustrated in FIG. 17A. The four tomographic images of the central cross-shape and upper-and-lower-line pattern are displayed in frames 530A, 530B, 530C, and 530D of the display 350. This allows the examiner to determine what 3D volume is imaged in the image capturing region 521. The main imaging scanning pattern is an example of the first scanning pattern for scanning the measurement light over the image capturing region of the subject eye E. The prescanning pattern 1 is an example of a second scanning pattern for scanning the measurement light over at least part of the image capturing region in a scanning time shorter than the scanning time of the first scanning pattern.

If the examiner determines that the OCT image capturing region needs to be changed (S150), the examiner can adjust the position and range of the image capturing region by dragging the indicator 521 indicating the OCT image capturing region with a pointing device (not illustrated) (S155). If the image capturing position is corrected, the SLO focusing is repeated.

Reference Light Path Length Adjustment

When the examiner presses a start button for reference light path length adjustment and OCT focus adjustment (550 in FIG. 4), the reference-light-path length control unit 310 in the control/signal processing unit 180 adjusts the reference light path length so that the individual tomographic images come to proper positions (for example, the tomographic images are positioned in the vicinity of the heightwise center of the frame 530A (S160). Of course, the examiner can manually adjust the reference light path length by operating a slide bar provided on the left of the frame 530A.

OCT Focusing

Upon completion of the reference light path length adjustment (for example, it is determined that the imaged position is at a predetermined depth in the frame), the OCT scanning control unit 309 repeatedly drives the OCT scanning unit in the prescanning pattern 2 for the following OCT focusing (S170). For example, if the main imaging scanning pattern is the rectangular 3D-volume scanning pattern 521, a diagonal scanning pattern in the OCT image capturing region (rectangular) as in FIG. 17A is selected for the prescanning pattern 2. The OCT focus lens 120 in the OCT unit is present in the vicinity of the OCT in-focus position because the OCT focus lens 120 has already been moved to a position corresponding to the SLO focus lens 210 at the SLO focusing.

The OCT focus control unit 311 drives the lens driving mechanism 125 to move the OCT focus lens 120 by a predetermined amount (−δF) from that position, thereafter repeatedly moves the lens driving mechanism 125 by a predetermined amount Δ in the reverse direction every scanning in the prescanning pattern 2, and evaluates OCT images corresponding to the prescanning pattern 2, generated by the OCT image generation unit 308, in sequence, to search for the in-focus position of the OCT unit (S180). Note that the repetition period of the prescanning pattern 2 (the diagonal scanning pattern of the OCT image capturing region (rectangular)), which is an example of the second scanning pattern, is set sufficiently shorter than the imaging period using the main imaging scanning pattern (the rectangular 3D volume scanning pattern), which is an example of the first scanning pattern. This allows OCT focusing in a predetermined time even if prescanning is repeated for focusing evaluation, reducing a burden on the examinee. FIG. 17A illustrates other prescanning patterns 2 corresponding to the main imaging scanning patterns together with the prescanning patterns 1.

Figure 6:
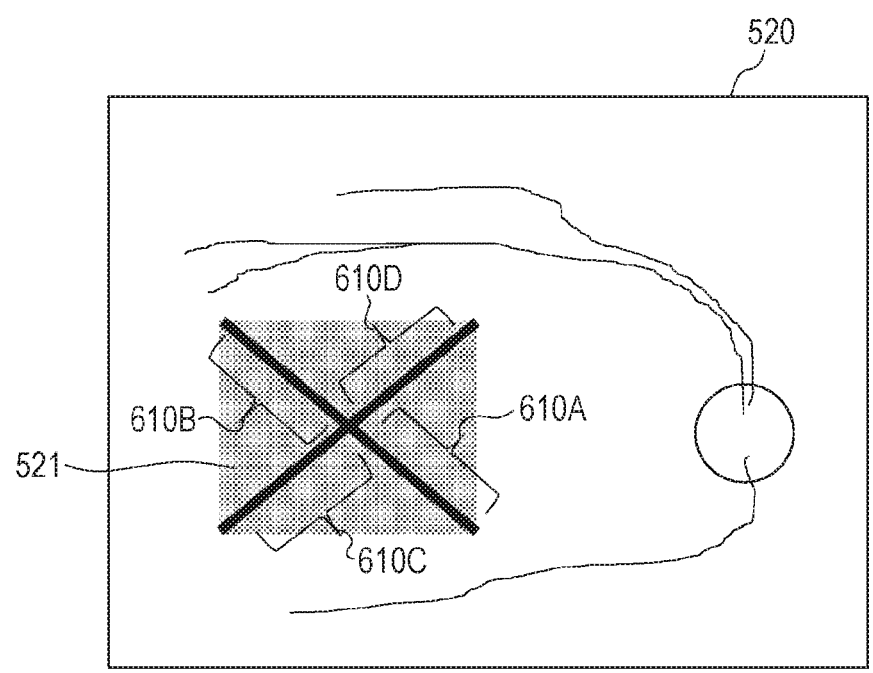
FIG. 6 is a diagram illustrating an example of a prescanning pattern 2 on the fundus.
Figure 7A:
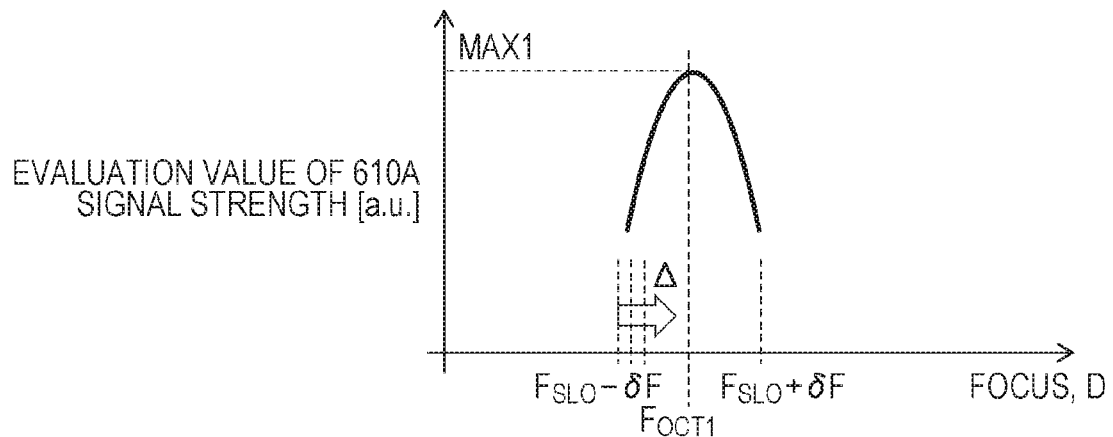
FIG. 7A is a diagram illustrating a change in an evaluation value indicating the in-focus state of OCT.
Figure 7B:
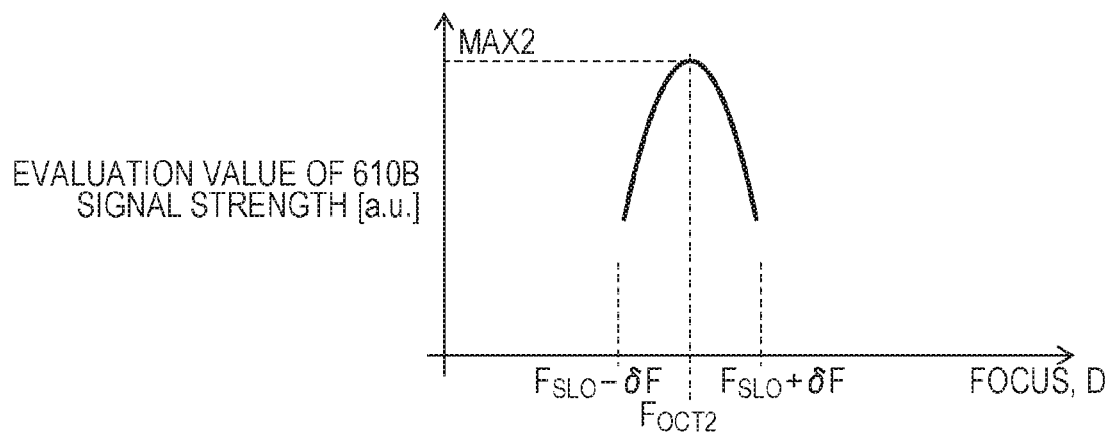
FIG. 7B is a diagram illustrating a change in an evaluation value indicating the in-focus state of OCT.
Figure 7C:
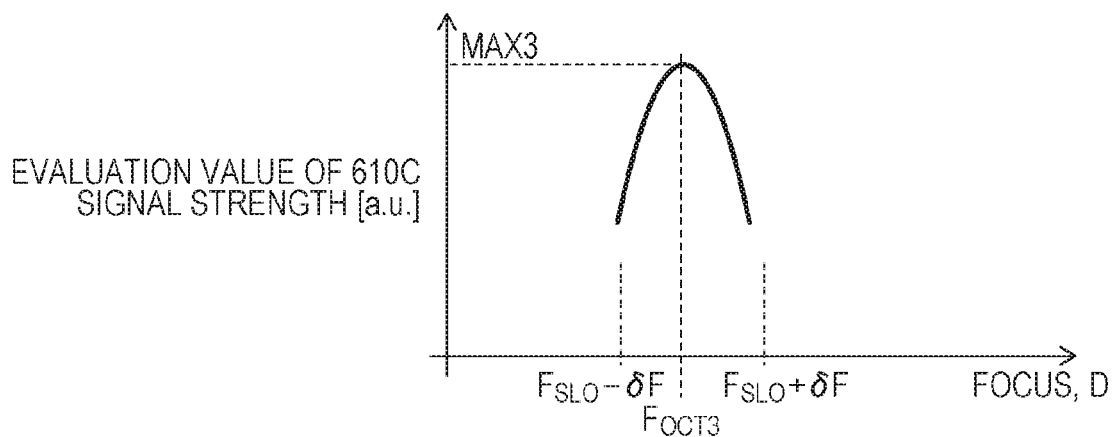
FIG. 7C is a diagram illustrating a change in an evaluation value indicating the in-focus state of OCT.
Figure 7D:
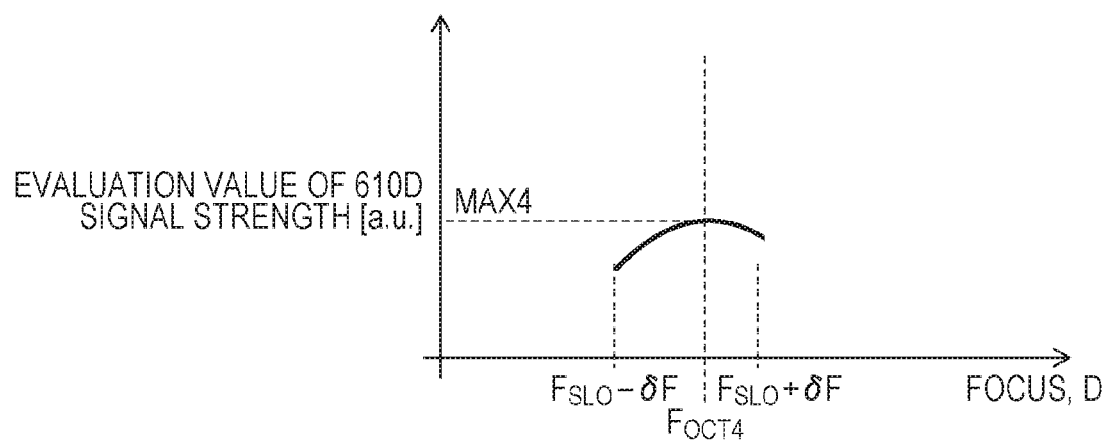
FIG. 7D is a diagram illustrating a change in an evaluation value indicating the in-focus state of OCT.

The actual diagonal scanning pattern on the fundus is divided into four portions 610A, 610B, 610C, and 610D, as illustrated in FIG. 6, for each of which evaluation is performed. For an evaluation function for OCT focusing, for example, the contrast of the OCT image of each portion or the amplitude/average luminance of high-luminance portions is used. To further reduce the focusing time, an evaluation function with low computational load using the variance of spectrometer output during scanning of the scanning lines may be used. Alternatively, the number of samples in the A-mode may be thinned out to further reduce the computation time.

Assuming that the amplitude/average luminance of the high luminance portions of the OCT image is used as the evaluation function, the OCT image generation unit 308 in the control/signal processing unit 180 obtains a depthwise luminance profile (an A-mode signal) from a signal output from the spectrometer 170 at a predetermined position on the prescanning pattern 2 at a given focal position. The OCT image generation unit 308 arrays luminance profiles obtained from a plurality of continuous positions to obtain a retina tomographic image corresponding to part of the prescanning pattern 2. The OCT image generation unit 308 extracts continuous regions with a predetermined luminance or higher of the tomographic image, that is, a portion in which the retina is present, and obtains the average luminance as the evaluation value for OCT focusing at the focal position in the predetermined region. If the prescanning pattern 2 is repeatedly scanned a plurality of times before the focal position is moved, the average may be calculated. The above procedure is repeated at different focal positions to search for an OCT in-focus position.

FIGS. 7A to 7D are graphs showing a change in evaluation value indicating the in-focus state of OCT relative to the position of the OCT focus lens 120. FIGS. 7A, 7B, 7C, and 7D show evaluation values corresponding to the portions 610A, 610B, 610C, and 610D, respectively. The evaluation values respectively have single peaks with maximum values of Max1, Max2, Max3, and Max4 at positions OCT1 to OCT4 of the OCT focus lens 120. The difference reflects the unevenness of the subject eye fundus and a subtle difference in the structure. The difference is small, and the evaluation values are almost the same when the subject eye is healthy. For this reason, when the positions OCT1 to OCT of the OCT focus lens 120 and the maximum values Max1 to Max4 at the peaks are within a predetermined range, the simple average of OCT1 to OCT4 is calculated as the in-focus position of the OCT. If the maximum value is significantly lower than the values of the other portions, or if the peak position differs, as in FIG. 7D, it is determined to be an abnormal value due to lesion or deformation and is preferably excluded from the averaging operation. Although the present embodiment shows a method of dividing the prescanning pattern 2 into four and determining the OCT in-focus position from the difference in the four evaluation values, the number of divided portions is not limited to four, and not the simply divided portions but a plurality of separate portions may be used. The advantageous effect of the present invention can be obtained in searching for an average in-focus position, even without division.

After completion of the OCT focusing, as described above, the OCT scanning control unit 309 in the control/signal processing unit 180 starts scanning of OCT using the prescanning pattern 1 again (S190) and waits for the start of image capturing (S195), wherein if the OCT image capturing region is changed, the processing returns to S155 to adjust the position and range of image capturing. When the examiner presses an imaging start button (560 in FIG. 4), the SLO unit starts to store an SLO image obtained by raster scanning (S200), obtains an OCT tomographic image according to the main imaging scanning pattern (S205), reconfigures the image, and stores the result of reconfiguration, and displays the result on the display 350 (S210). This is a procedure for imaging and image reconfiguration. The examiner checks the image capturing result on the display 350 (S215), wherein if image recapturing is needed, the examiner presses a cancel button 570 to return to S140, whereas there is no problem in the result, the examiner presses a completion button 580 to store the image (S220), and the image capturing ends.

Thus, the apparatus of the present embodiment provides efficient focusing of the OCT unit, providing a high-quality OCT image.

Modifications

The repetition period of scanning in the prescanning pattern 2 needs to be sufficiently shorter than the imaging period using the main imaging scanning pattern, as described above. In addition, the scanning pattern preferably makes it easy to detect the focus state of the entire main scanning region.

Figure 8:
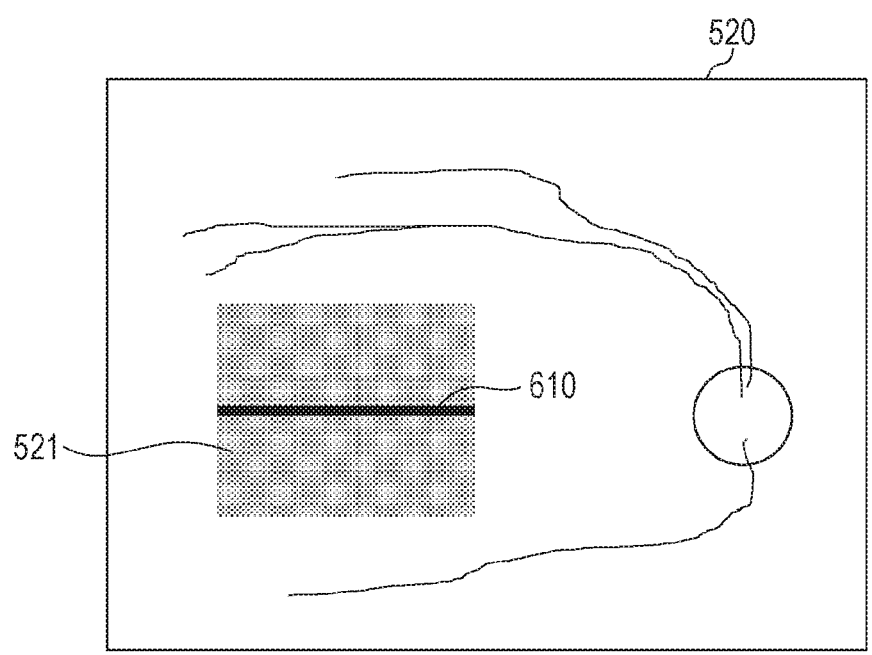
FIG. 8 is a diagram illustrating another embodiment of the prescanning pattern 2 on the fundus.
Figure 9:
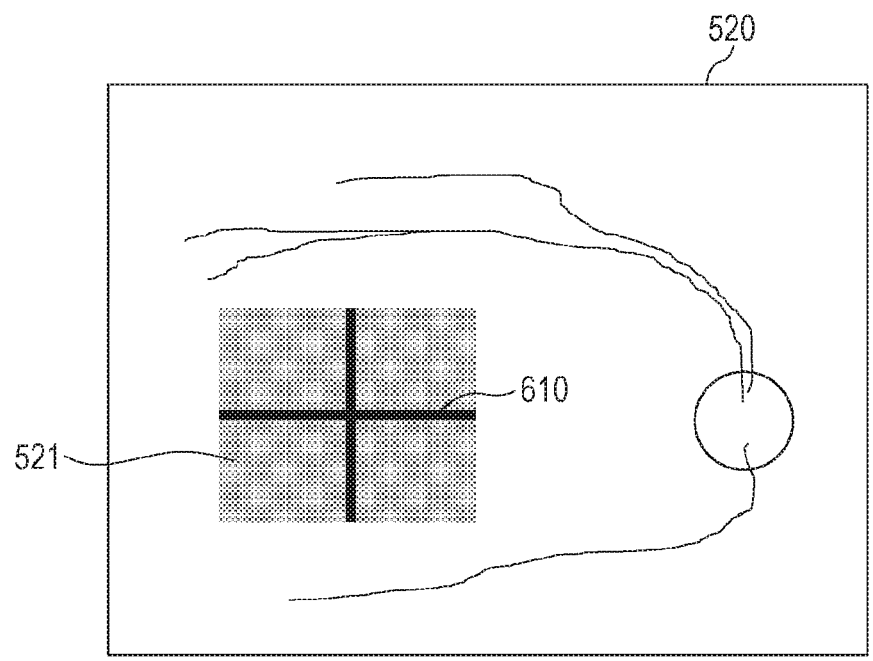
FIG. 9 is a diagram illustrating still another embodiment of the prescanning pattern 2 on the fundus.
Figure 10:
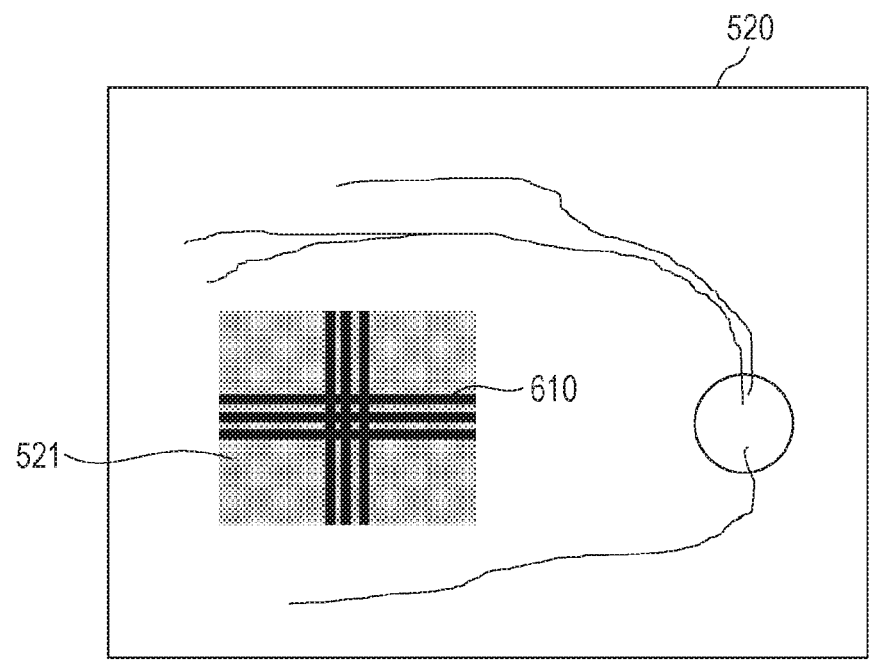
FIG. 10 is a diagram illustrating still another embodiment of the prescanning pattern 2 on the fundus.

An example of the simplest prescanning pattern 2 is a horizontal line 610 at the center of the image capturing region 521, as illustrated in FIG. 8. This is applicable when the OCT image itself is used for a normal subject in evaluation of OCT focusing and when the A scan density is equal to the density of main imaging to observe a correct in-focus state, that is, when it takes much time to calculate the focusing evaluation value. Of course, vertical and horizontal cross-shape scanning, as in FIG. 9, and scanning in the directions of multiple crosses, as in FIG. 10, may be performed by decreasing the A scanning density. The cross-shaped scanning is to scan the measurement light over a cross-shaped character passing through the center of the image capturing region and composed of two lines parallel to two sides.

Figure 11:
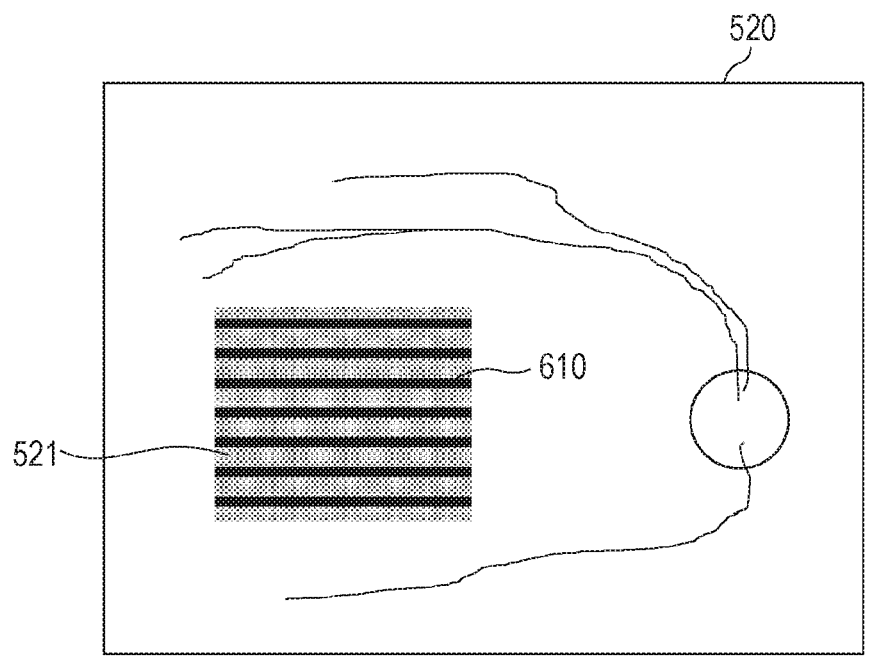
FIG. 11 is a diagram illustrating still another embodiment of the prescanning pattern 2 on the fundus.

When the retina of the subject eye E obviously has unevenness, so that evaluation of focusing of the entire image capturing region is needed, a method that does not take much time to calculate the focusing evaluation value may be selected, in which a prescanning pattern for raster-scanning the entire image capturing region at a low scanning density, as in FIG. 11, is selected.

Figure 12:
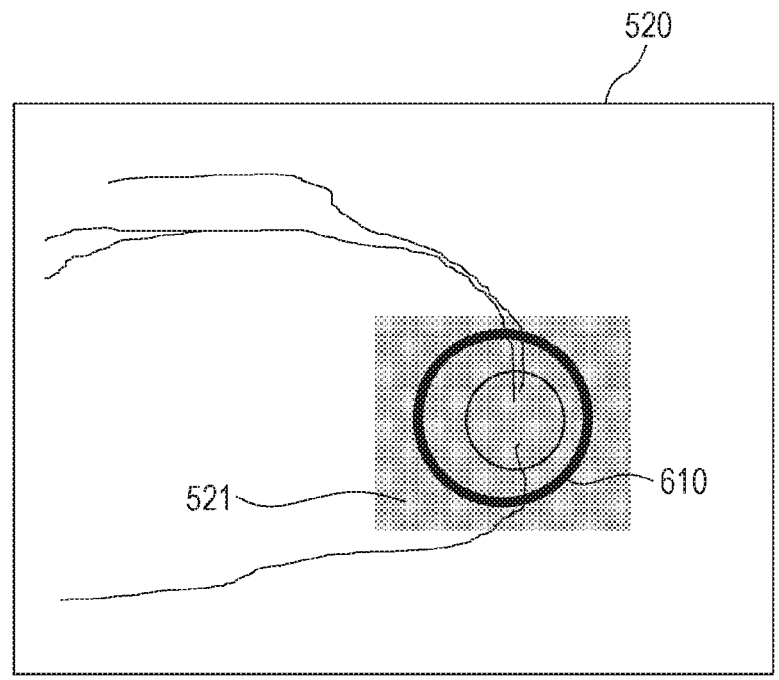
FIG. 12 is a diagram illustrating still another embodiment of the prescanning pattern 2 on the fundus.
Figure 13:
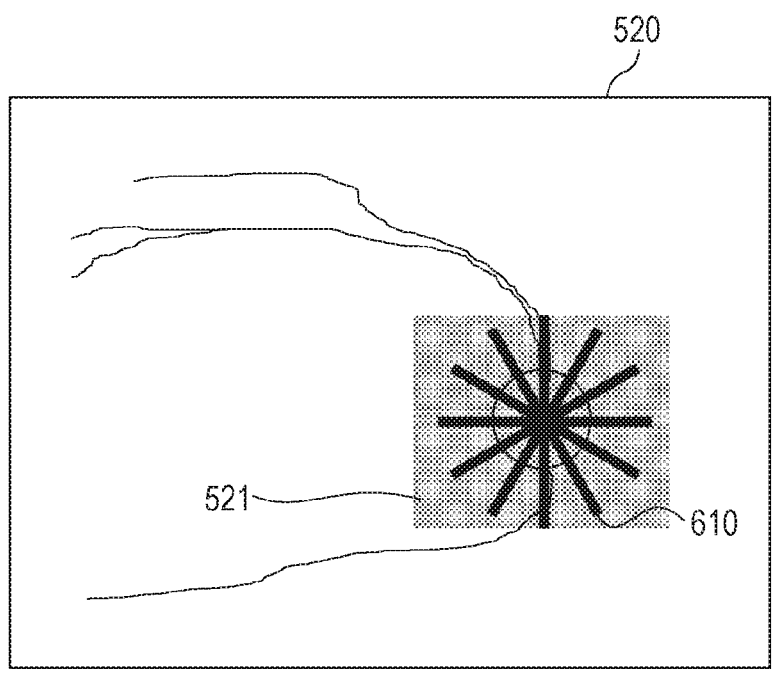
FIG. 13 is a diagram illustrating still another embodiment of the prescanning pattern 2 on the fundus.

In the case where the object to be imaged includes a nipple, circular scanning, as in FIG. 12, or radial scanning, as in FIG. 13, is preferable. For the circular scanning, the diameter is preferably between one half and three fourths of the maximum width of the image capturing region, or double circle scanning is preferable for efficient focusing evaluation.

These are modifications of the prescanning pattern 2 applicable to the present invention. It is to be understood that the scanning patterns may be switched according to the operator's discretion or depending on the site to be imaged. It is also to be understood that a combination of these patterns may be used.

Second Embodiment

Line-Scanning OCT Apparatus

Figure 14:
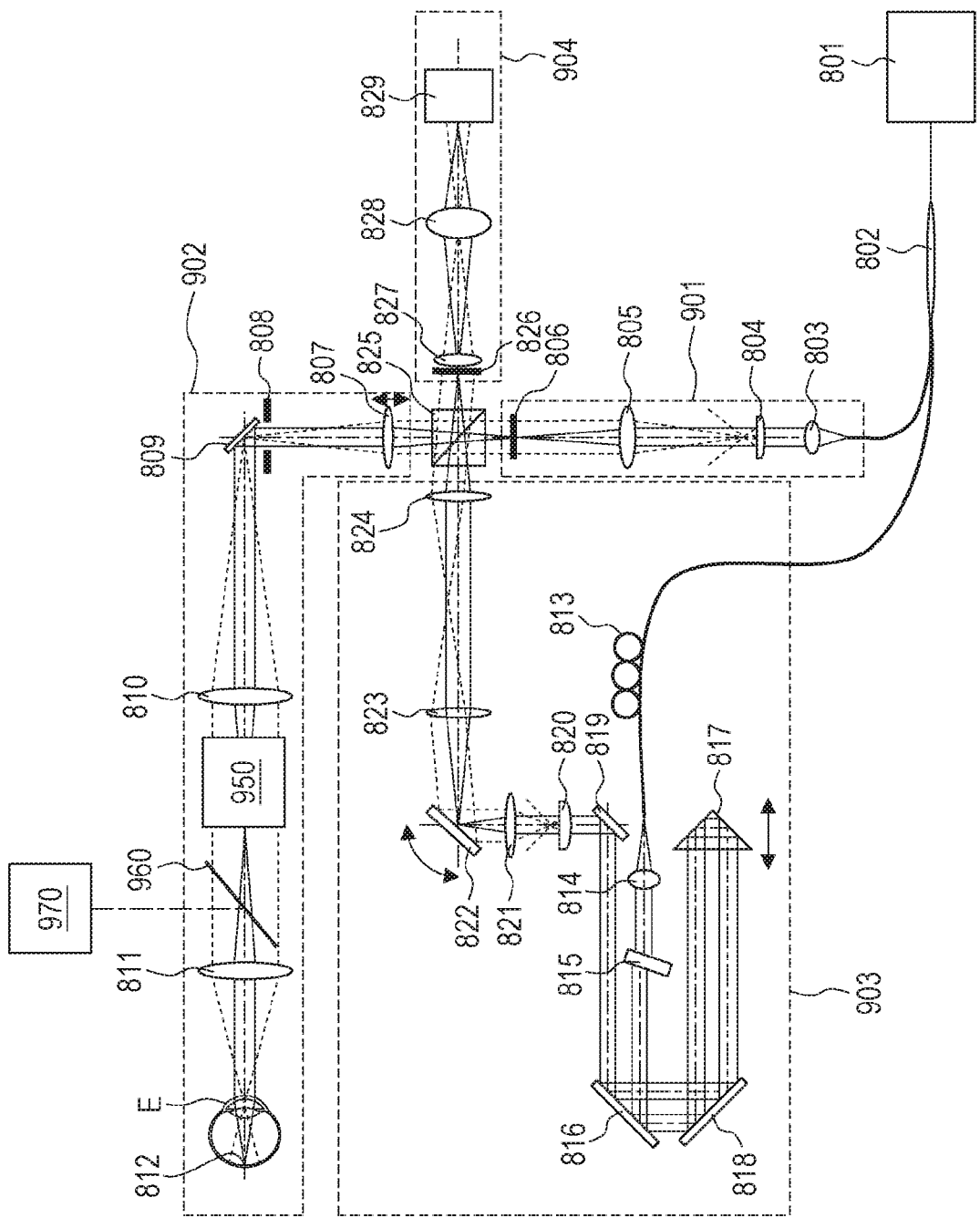
FIG. 14 is a diagram illustrating the configuration of a line-scanning swept source (SS)-OCT apparatus.

Although the configuration of the OCT apparatus according to an embodiment of the present invention has been described taking the SD-OCT as an example with reference to FIG. 1, an OCT apparatus to which the present invention is applicable is not limited to the SD-OCT. For example, a swept source (SS)-OCT may be configured by replacing the light source in FIG. 1 with a wavelength swept light source, replacing the spectrometer 170 with a high-sensitivity light-receiving element, and sampling its outputs with a wave number based on the sweep wavelength of the light source. The present invention may be applied not only to the two-dimensional scanning type illustrated in FIG. 1 but also to a line scanning OCT apparatus (that scans measurement light radiated in a line pattern over the image capturing region in a one-dimensional pattern), illustrated in FIG. 14. The two-dimensional scanning type scans measurement light radiated in a dot pattern in the image capturing region. An example of the line scanning OCT apparatus will be described hereinbelow with reference to FIG. 14.

A light source 801 is a wavelength swept light source. The measurement light emitted from the light source 801, the wavelength of which is repeatedly swept, is split into measurement light and reference light by an optical coupler 802, which is a light splitting unit.

The obtained measurement light is guided to a line-image forming optical system 901, in which the measurement light is collimated by a lens 803 and forms a line image on a plane 806 through a cylindrical lens 804 and a lens 805. In the drawing, the solid lines indicate light beams focused on the plane 806 in the sagittal direction perpendicular to the plane of the drawing, and the broken lines indicate light beams collimated on the plane 806 in the tangential direction parallel to the plane of the drawing.

The measurement light further passes through a beam splitter 825 into a sample optical system 902. The sample optical system 902 includes an OCT focus lens 807, an aperture 808, a galvanometric mirror 809, which is an optical scanning unit disposed at a position substantially conjugate to the anterior part of the subject eye E, and lenses 810 and 811 forming an objective lens system, which guide the measurement light to a subject eye fundus 812 to form a line image on the fundus. Between the lens 810 and the lens 811, an image rotator 950 is disposed, so that the line image formed on the subject eye fundus 812 can be rotated in any direction.

The OCT focus lens 807 moves on the optical axis so that the plane 806 and the fundus 812 of the subject eye E become optically conjugate, as in the first embodiment. The position of the OCT focus lens 807 is adjusted to an in-focus state, and then the galvanometric mirror 809 is moved. This allows a line image formed of the measurement light guided onto the fundus 812 to be moved in the direction perpendicular to the line. Continuously scanning the line allows three-dimensional scanning over the fundus 812, like raster scanning, as in FIG. 11. Meanwhile, driving the image rotator 950 allows the line image formed of the measurement light guided onto the fundus 812 to be rotated, and intermittently scanning the line allows radial scanning over the fundus 812, as in FIG. 13.

The measurement light reflected and scattered by the fundus 812 of the subject eye passes through the sample optical system 902 and is reflected by the beam splitter 825 into an image capturing system 904, in which a line image of the measurement light is formed on a plane 826 (described below).

The image capturing system 904 includes the plane 826, which is optically conjugate to the fundus 812 of the subject eye E and the plane 806. Furthermore, the plane 826 is conjugate also to the light-receiving surface of a line sensor 829 via a lens 827 and a lens 828. This allows the measurement light reflected and scattered from the line image on the fundus 812 to reach the line sensor 829.

The reference light is guided to a reference system 903, where the reference light is collimated to collimated light by a collimator lens 814 and is attenuated to a predetermined amount of light through a neutral density (ND) filter 815. Thereafter, the reference light is reflected by a mirror 816 and a mirror 818 while keeping its collimated state, is turned back by a reference mirror 817, which is movable on the optical axis and capable of correcting a difference in optical path length from the sample optical system 902, and is reflected by the mirrors 818 and 816 and a mirror 819. The reference light further passes through a line-image forming lens system including a cylindrical lens 820 and a lens 821 to form a line image, or an intermediate image, on a mirror 822. The intermediate line image passes through a lens 823, a lens 824, and the beam splitter 825 to form a line image of the reference light onto the plane 826.

In other words, the reference light and the measurement light are multiplexed by the beam splitter 825, and the line image of the reference light and the line image of the measurement light interfere with each other on the plane 826, as described above. The interfered line image is received by the line sensor 829 and is output as an output signal.

The reference system 903 includes a polarization adjusting paddle 813 in which optical fibers are bound to multiple rings and a polarization adjustment driving unit (not illustrated) so as to adjust the polarization state of the reference light relative to the polarization state of the measurement light to improve the interference between the measurement light and the reference light.

In addition, driving of the OCT focus lens 825, the galvanometric mirror 809, and the reference mirror 817 is performed by the control/signal processing unit 180, as in the first embodiment.

Fundus Observation Unit

A dichromatic mirror 960 is disposed between the two lenses 810 and 811 constituting an objective lens system. Furthermore, an SLO unit 970 serving as a fundus observation unit is provided on a branch optical path, as in FIG. 1.

OCT Image Reconfiguration

The line sensor 829 repeatedly performs an exposing operation and a reading operation at one drive position of the optical scanning unit 140 at regular wavenumber intervals corresponding to the wave sweep of the wave swept light source 801. The read outputs are sampled by the second A/D converter 307 in the control/signal processing unit 180 and stored in the image memory 304 as an interference signal set serving as the source of depth information obtained by being sampled at predetermined wavenumber intervals for each of the pixels of the line sensor 829. By repeating the obtaining of the interference signal set while controlling the scanning position of the optical scanning unit 140, a three-dimensional tomographic signal composed of multiple scanning lines is obtained. The OCT image generation unit 308 generates a tomographic image of the subject eye fundus at the scanning position of the optical scanning unit 140 by operating these interference signal sets for each interference signal corresponding to corresponding one of pixels of the line sensor 829.

A description of an operational procedure for the line scanning OCT apparatus with the above configuration will be omitted. The procedure is basically similar to that of the first embodiment illustrated in FIG. 3. A difference is that all of the prescanning pattern 1, the prescanning pattern 2, and the main scanning pattern are limited to one or a combination of scanning patterns corresponding to the line sensor 829. FIG. 17B illustrates examples of scanning patterns that may be effective in the present embodiment. The scanning lines other than a horizontal scanning line, such as the diagonal scanning line and the cross-shaped scanning line, may be changed in angle on the fundus by driving the image rotator 950.

Thus, the present invention is effectively applicable also to the line scanning OCT apparatus, providing efficient focusing of the OCT unit, providing a high-quality OCT image.

Third Embodiment

Application to OCTA

Figure 15:
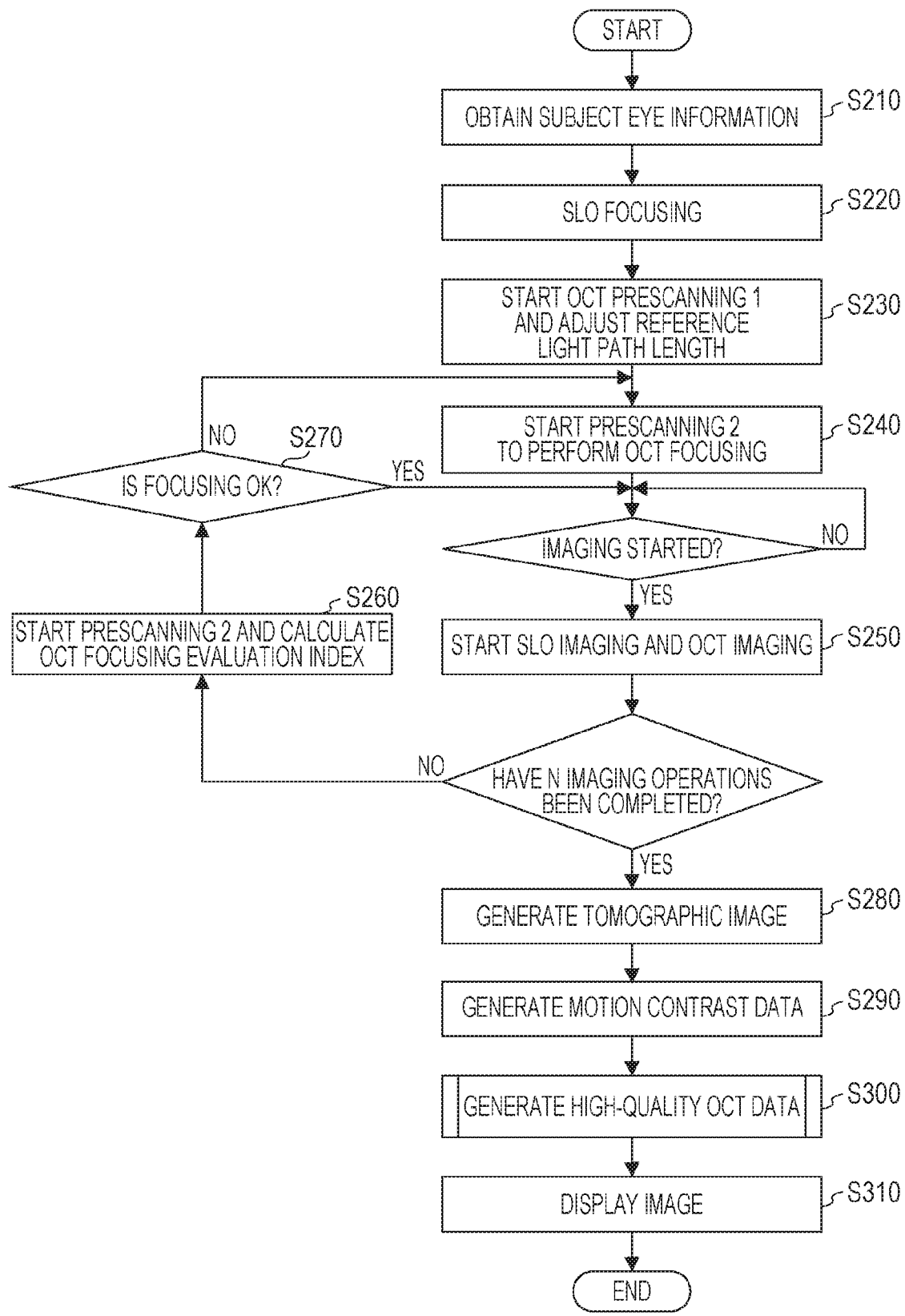
FIG. 15 is a flowchart for an OCTA imaging procedure.

In recent years, OCT angiography (OCTA) using no contrast material has been proposed as a new application of the OCT. The OCTA is an imaging technique for repeatedly capturing an image of the same cross section (the same portion) of the object to be imaged using the OCT to generate data, or motion contrast data, on the temporal change of the object during the image capturing, for example, temporal changes in phase, vector, and intensity of the complex OCT signal, from the difference, ratio, or correlation, and finally projecting the obtained three-dimensional motion contrast data onto a two-dimensional plane to generate a blood vessel image (hereinafter referred to as "OCTA image"). Since the OCTA image is thus generated from a plurality of pieces of image data by multiple steps of computational processing, the image quality of the underlying OCT signals has a significant influence on the final result. It will be appreciated that the in-focus state of the OCT unit is also a major factor affecting the image quality. Thus, the present invention particularly offers its effect to OCTA imaging. Another method for improving the quality of the OCTA image has been proposed in which a plurality of OCTA images are separately obtained, then the images are aligned, and the average is calculated. In such an imaging technique, OCTA image capturing of the same cross section in the OCT is further repeated a plurality of times. This increases the total imaging period, thus significantly increasing a burden on the subject, as well as on the examiner. For this reason, how to reduce the total imaging period is a major issue. FIG. 15 illustrates a procedure for OCTA imaging to which the present invention is effectively applied in a sequence of separately capturing a plurality of OCTA images using the SD-OCT apparatus illustrated in FIG. 1.

In the present embodiment, a scanning pattern for OCTA imaging is a three-dimensional volume scanning pattern (300×300) using raster scanning. Since the same scanning line is repeatedly scanned M times (M is equal to or greater than 2) to calculate the motion contrast, a data quantity of 300×300×M is actually captured at one OCTA imaging. In the present embodiment, the main imaging is repeated N times (N is equal to or greater than 2) to generate high-image-quality data, and as a result, a data quantity of 300×300×M×N is captured in total. Since the apparatus of the present embodiment obtains the above quantity of data properly from the same position for averaging of the OCTA, tracking of the subject eye E is preferably performed (a detailed description is omitted). The tracking allows providing a high-quality OCTA image less affected by involuntary eye movement. If an artifact motion, such as blinking, is detected in generating an image, automatic rescanning at the site of the artifact may sufficiently decrease the probability of imaging failure.

When the power source of the apparatus is turned on, driving of the SLO unit is normally started. At S210, a subject-eye-information obtaining unit (not illustrated) obtains a subject identification number from the outside to ensure identification of a plurality of pieces of OCTA data to be captured. This subject eye identification information is stored in an external storage apparatus (not illustrated) later, together with the eye type, the left eye or the right eye, to be recognized by the apparatus and the OCTA image data.

Figure 3:
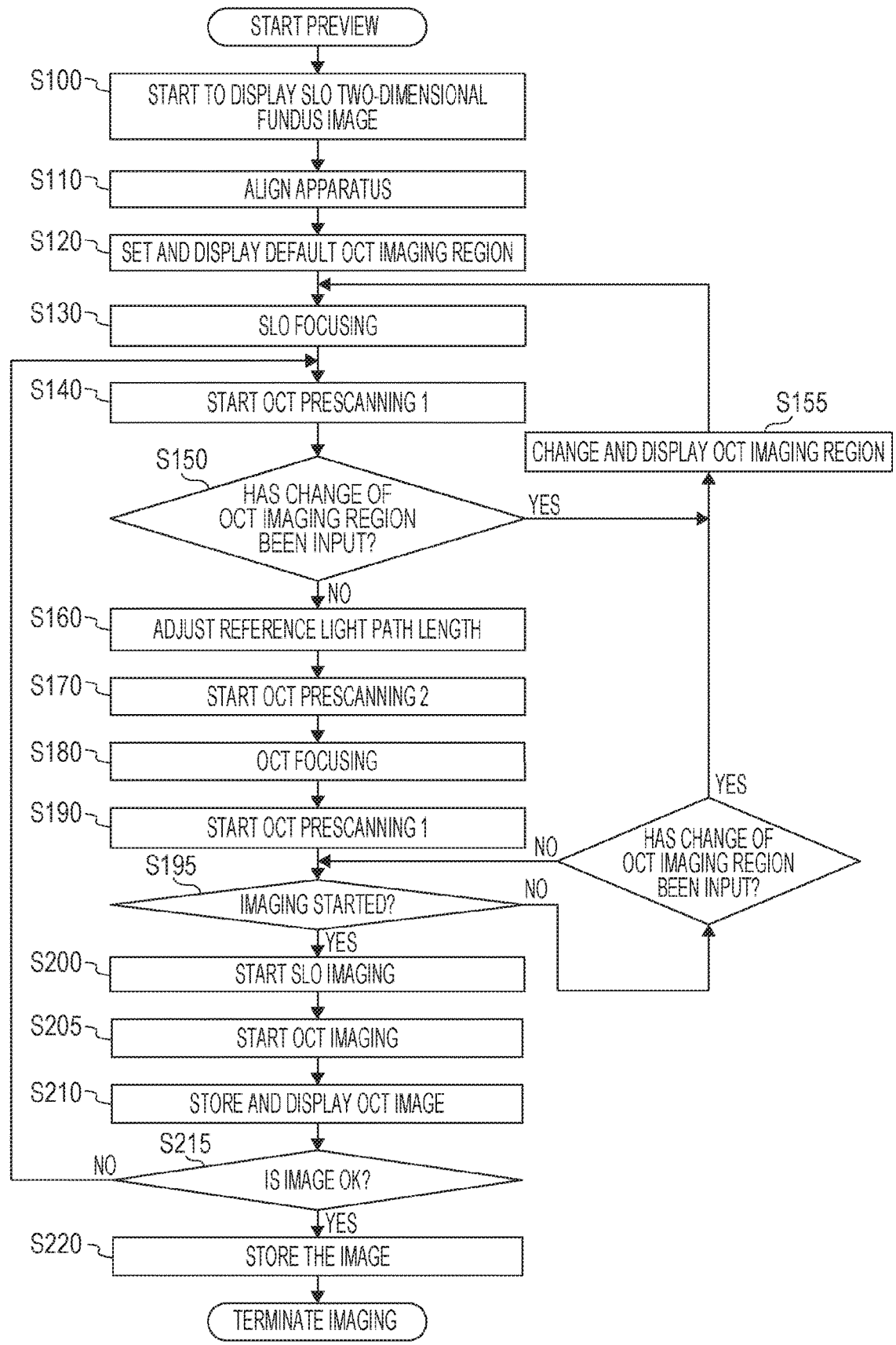
FIG. 3 is a flowchart for an OCT imaging procedure.
Figure 4:
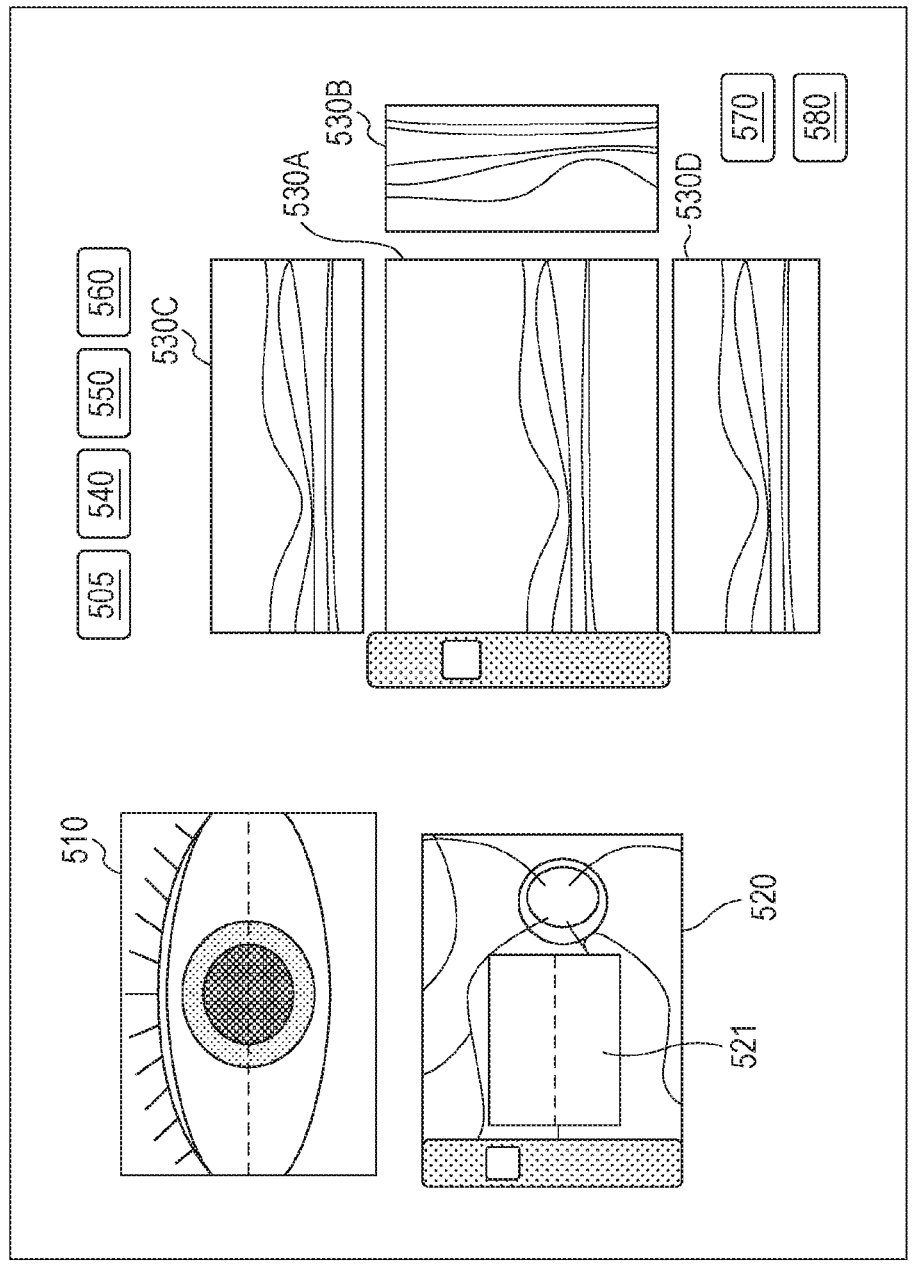
FIG. 4 is a diagram illustrating a display screen.

Thereafter, the control/signal processing unit 180 performs an SLO focusing operation (S220), as in the first embodiment illustrated in FIG. 3. After completion of the SLO focusing, then at S230, the OCT unit starts OCT scanning using the prescanning pattern 1, and the control/signal processing unit 180 adjusts the reference light path length so that the individual tomographic images come to proper positions (for example, the tomographic images come to the vicinity of the heightwise center of the frame 530A).

After completion of the reference light path length adjustment, the OCT unit repeatedly drives the OCT scanning unit to perform OCT focusing using the prescanning pattern 2 for OCT focusing (S240). After completion of the adjustment of the imaging parameters, the operator issues an instruction to start imaging, SLO imaging and one OCTA imaging are started (S250). This OCTA imaging is repeated predetermined N times. The above operating procedure is substantially the same as the procedure of the first embodiment except that a repeated scanning pattern for OCTA is employed as the main scanning pattern.

During the repeated operation, the control/signal processing unit 180 checks a change in in-focus state at S300, with the OCT focus lens 120 kept undriven. In other words, the control/signal processing unit 180 repeatedly operates the OCT scanning unit using the prescanning pattern 2 for OCT focusing, calculates an evaluation value (an evaluation index) for evaluating the in-focus state from the corresponding OCT images (S260), and compares the calculated evaluation value and a threshold (S270). If the evaluation value >the threshold (the evaluation value is greater than the threshold), the control/signal processing unit 180 determines that the in-focus state is kept good and skips the OCT focusing operation (S240) and waits for an imaging start instruction again. If the evaluation value <the threshold (the evaluation value is smaller than the threshold), the control/signal processing unit 180 determines that the state of the subject eye E has changed into a poor focus state and returns to the OCT focusing (S240). In other words, the control/signal processing unit 180, which is an example of the calculation unit, calculates the motion contrast a plurality of times (obtains N OCTA images), and calculates an evaluation index for evaluating the in-focus state of the focusing unit using the output from the light receiving unit during the period in which the measurement light is repeatedly scanned using the second scanning pattern corresponding to (immediately before) the first scanning pattern, for calculating the motion contrast after the second imaging. If the calculated evaluation index is smaller than the threshold, the control/signal processing unit 180, which is an example of the control unit, controls the driving unit to drive the focusing unit.

Upon completion of N times of OCTA imaging, the processing proceeds to step S280, in which OCT image reconfiguration is performed. At the next step S290, a motion-contrast data calculation unit of the OCT image generation unit 308 in the control/signal processing unit 180 generates motion contrast data, which is OCTA-specific data.

Figure 16:
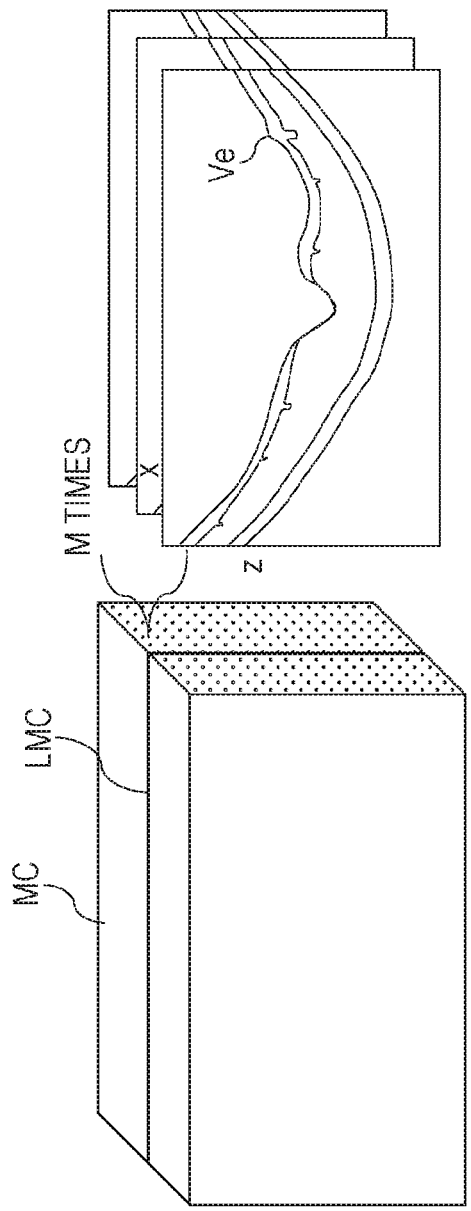
FIG. 16 is a diagram illustrating generation of motion contrast data.

The generation of this data will be briefly described with reference to FIG. 16. MC denotes three-dimensional motion contrast data, and LMC denotes two-dimensional motion contrast data constituting the three-dimensional motion contrast data. A method for generating the LMC will be described.

The motion-contrast data calculation unit first corrects the positional misalignment among a plurality of tomographic images captured in the same region of the subject eye E. Any method may be used to correct the positional misalignment. For example, the motion-contrast calculation unit aligns M pieces of tomographic image data corresponding to the same region using the feature, such as the shape of the fundus. Specifically, the motion-contrast calculation unit selects one of the selected M pieces of tomographic image data as a template and determines the similarity to the other tomographic image data while changing the position and angle of the template to obtain the amount of positional misalignment with respect to the template. Thereafter, the motion-contrast calculation unit corrects each tomographic image data based on the amount of positional misalignment obtained.

Next, the motion-contrast data calculation unit determines a decorrelation value D between two pieces of tomographic image data obtained at continuous imaging times. The decorrelation value D increases as the difference between two luminance values and is generally set at 0 to 1. If the repetition time M at the same position is three or more, the motion-contrast data calculation unit can obtain a plurality of decorrelation values $D(x, z)$ at the same position $(x, z)$. The motion-contrast calculation unit can generate final motion contrast data by performing statistical processing, such as calculation of the maximum value or the average of the plurality of decorrelation values $D(x, z)$. If the repetition time M is 2, such statistical processing such as the calculation of the maximum value or averaging calculation, is not performed, and the decorrelation value $D(x, z)$ between two adjacent tomographic images A and B is used as the motion contrast value at the position $(x, z)$.

The decorrelation value D generally tends to be affected by noise. For example, if the plurality of pieces of tomographic image data has noise at no-signal portions, whose values differ from each other, the decorrelation value D increases, and the noise superposes on the motion contrast data. To prevent it, the motion-contrast data calculation unit performs preprocessing of replacing tomographic data below a predetermined threshold, regarding such tomographic data as zero. This allows the OCT image generation unit 308 to generate three-dimensional motion contrast data MC in which influence of noise is reduced based on the preprocessed tomographic data.

At the following step S300, the OCT image generation unit 308 generates high-quality OCTA data by aligning the positions of the plurality of pieces of motion contrast data MC in which the influence of noise is reduced and by performing an averaging operation. There are a plurality of methods for obtaining a high-quality OCTA image. Examples include a method of projecting one piece of three-dimensional motion contrast data MC' obtained by three-dimensionally aligning a plurality of pieces of three-dimensional motion contrast data MC and performing an averaging operation thereon onto a two-dimensional plane and a method of averaging a plurality of OCTA images obtained by projecting each of a plurality of pieces of three-dimensional motion contrast data MC onto a two-dimensional plane (the details are omitted).

At step S310, the high-quality OCTA image generated by averaging operation is displayed on the display 350. For example, if the high-quality OCTA image is to be displayed using the method of aligning a plurality of pieces of three-dimensional motion contrast data MC in a three dimensional manner and thereafter averaging them, motion contrast data corresponding to the region between the upper end and the lower end of a generation region specified for the averaged three-dimensional motion contrast data is projected onto a two-dimensional plane to generate an OCTA image, and the OCTA image is displayed. Alternatively, the averaged three-dimensional motion contrast data may be subjected to volume rendering and may be displayed in a three-dimensional manner.

The above configuration of the present embodiment allows reliable checking of the in-focus state of the OCT unit during the repeated OCTA imaging, providing a high-quality OCTA image in a short time.

Other Embodiments

Embodiments of the present invention can also be realized by executing the following processes. The processes are executed by providing software (programs) for implementing the functions of the embodiments to a system or an apparatus via a network or various storage media and by reading the programs with a computer (or a central processing unit [CPU] or a micro processing unit [MPU]) of the system or the apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An optical coherence tomography apparatus comprising:
    an interference optical system including a light receiving unit configured to receive interference light of returned light from a subject eye irradiated with measurement light and reference light corresponding to the measurement light;
    a tomographic-image obtaining unit configured to obtain a tomographic image of the subject eye using an output from the light receiving unit;
    an optical scanning unit disposed in the interference optical system and configured to scan the subject eye with the measurement light;
    a driving unit disposed in the interference optical system and configured to drive a focusing unit; and
    a control unit configured, before a tomographic image to be stored is obtained using the output from the light receiving unit during a period in which the measurement light is scanned in a first scanning pattern for scanning an image capturing region of the subject eye, to control the optical scanning unit so as to repeatedly scan the measurement light in a second scanning pattern for scanning the measurement light over at least part of the image capturing region in a scanning time shorter than a scanning time of the first scanning pattern and to control the driving unit so as to drive the focusing unit using the output from the light receiving unit during a period in which the measurement light is repeatedly scanned in the second scanning pattern.

2. The optical coherence tomography apparatus according to claim 1, wherein the optical scanning unit scans the measurement light in a dotted or line shape over the image capturing region.

3. The optical coherence tomography apparatus according to claim 1, wherein the second scanning pattern has a scanning density lower than a scanning density of the first scanning pattern.

4. The optical coherence tomography apparatus according to claim 1, wherein the second scanning pattern is a scanning pattern for scanning the measurement light over part of the image capturing region.

5. The optical coherence tomography apparatus according to claim 1, wherein the second scanning pattern is a scanning pattern for scanning the measurement light along one line passing through a center of the image capturing region.

6. The optical coherence tomography apparatus according to claim 1,
    wherein the image capturing region is rectangular, and
    wherein the second scanning pattern is a scanning pattern for scanning the measurement light along at least part of at least one diagonal of the image capturing region.

7. The optical coherence tomography apparatus according to claim 1,
    wherein the image capturing region is rectangular, and
    wherein the second scanning pattern is a scanning pattern for scanning the measurement light on a cross shape passing through the center of the image capturing region and including two lines parallel to two sides of the image capturing region.

8. The optical coherence tomography apparatus according to claim 1, wherein the second scanning pattern is a scanning pattern for scanning the measurement light over a circular shape including part of the image capturing region.

9. The optical coherence tomography apparatus according to claim 8, wherein the circular shape to be scanned has a diameter between one half and three fourths (both inclusive) of a maximum width of the image capturing region.

10. The optical coherence tomography apparatus according to claim 1, further comprising:
    a calculation unit configured to calculate motion contrast of the image capturing region using an output from the light receiving unit during a period in which the measurement light is repeatedly scanned over a same portion of the image capturing region a plurality of times as the first scanning pattern.

11. The optical coherence tomography apparatus according to claim 10, wherein the calculation unit calculates the motion contrast a plurality of times and calculate an evaluation index for evaluating an in-focus state obtained by the focusing unit using an output from the light receiving unit in a period in which the measurement light is repeatedly scanned in the second scanning pattern corresponding to the first scanning pattern, the second scanning patter being for calculating the motion contrast at second and subsequent calculations, and wherein the control unit controls the driving unit so as to drive the focusing unit if the calculated evaluation index is smaller than a threshold.

12. A method for controlling an optical coherence tomography apparatus including:

an interference optical system including a light receiving unit configured to receive interference light of returned light from a subject eye irradiated with measurement light and reference light corresponding to the measurement light;

a tomographic-image obtaining unit configured to obtain a tomographic image of the subject eye using an output from the light receiving unit;

an optical scanning unit disposed in the interference optical system and configured to scan the subject eye with the measurement light; and a driving unit disposed in the interference optical system and configured to drive a focusing unit, the method comprising the steps of:

controlling the optical scanning unit so as to repeatedly scan the measurement light in a second scanning pattern for scanning the measurement light over at least part of the image capturing region in a scanning time shorter than a scanning time of the first scanning pattern before a tomographic image to be stored is obtained using the output from the light receiving unit during a period in which the measurement light is scanned in a first scanning pattern for scanning an image capturing region of the subject eye; and controlling the driving unit so as to drive the focusing unit using the output from the light receiving unit during a period in which the measurement light is repeatedly scanned in the second scanning pattern.

13. A non-transitory computer-readable storage medium storing a program for causing a computer to execute the method for controlling the optical coherence tomography apparatus according to claim 12.

* * * * *